(12) United States Patent
Monsees et al.

(10) Patent No.: US 8,915,254 B2
(45) Date of Patent: Dec. 23, 2014

(54) METHOD AND SYSTEM FOR VAPORIZATION OF A SUBSTANCE

(75) Inventors: James Monsees, San Francisco, CA (US); Adam Bowen, San Francisco, CA (US)

(73) Assignee: Ploom, Inc., San Francisco, CA (US)

( * ) Notice: Subject to any disclaimer, the term of this patent is extended or adjusted under 35 U.S.C. 154(b) by 1429 days.

(21) Appl. No.: 12/482,376

(22) Filed: Jun. 10, 2009

(65) Prior Publication Data

US 2009/0260641 A1    Oct. 22, 2009

Related U.S. Application Data

(62) Division of application No. 11/485,168, filed on Jul. 11, 2006.

(60) Provisional application No. 60/700,105, filed on Jul. 19, 2005.

(51) Int. Cl.
*A24F 47/00* (2006.01)
*A24D 1/14* (2006.01)

(52) U.S. Cl.
CPC ............. *A24F 47/006* (2013.01); *A24D 1/14* (2013.01)
USPC ........... 131/273; 131/196; 131/194; 131/336; 131/335; 131/364

(58) Field of Classification Search
None
See application file for complete search history.

(56) References Cited

U.S. PATENT DOCUMENTS

| | | | |
|---|---|---|---|
| 968,160 A | 8/1910 | Johnson | |
| 2,104,266 A | 1/1938 | McCormick | |
| 2,830,597 A * | 4/1958 | Kummli | 131/273 |
| 2,935,987 A | 5/1960 | Ackerbauer | |
| 3,258,015 A | 5/1966 | Ellis et al. | |
| 3,292,634 A | 12/1966 | Beucler | |
| 3,479,561 A | 11/1969 | Janning | |
| 3,792,704 A | 2/1974 | Parker | |
| 4,020,853 A | 5/1977 | Nuttall | |
| 4,066,088 A | 1/1978 | Ensor | |
| 4,215,708 A | 8/1980 | Bron | |
| 4,219,032 A | 8/1980 | Tabatznik et al. | |

(Continued)

FOREIGN PATENT DOCUMENTS

| | | |
|---|---|---|
| CN | 1122213 A | 5/1996 |
| CN | 1333657 A | 1/2002 |

(Continued)

OTHER PUBLICATIONS

Bombick et al., Chemical and biological studies of a new cigarette that primarily heats tobacco. Part 2. In vitro toxicology of mainstream smoke condensate. Food and Chemical Toxicology. 1997; 36:183-190.

(Continued)

*Primary Examiner* — Richard Crispino
*Assistant Examiner* — Phu Nguyen
(74) *Attorney, Agent, or Firm* — Wilson Sonsini Goodrich & Rosati

(57) ABSTRACT

A smoking device for generating and releasing smoking vapor free from contamination into the mouth of a user comprising a mouthpiece for providing vapor for inhalation to a user including a tubular casing containing a heater for heating a smoking substance at a substantially constant low temperature by regulating the flow of fuel by a thermal regulator and further having means for visual indication of the operation of the device.

9 Claims, 3 Drawing Sheets

(56) References Cited

U.S. PATENT DOCUMENTS

| | | | |
|---|---|---|---|
| 4,506,683 | A * | 3/1985 | Cantrell et al. ............. 131/336 |
| 4,595,024 | A | 6/1986 | Greene et al. |
| 4,708,151 | A | 11/1987 | Shelar |
| 4,793,365 | A | 12/1988 | Sensabaugh, Jr. et al. |
| 4,794,323 | A | 12/1988 | Zhou et al. |
| 4,819,665 | A | 4/1989 | Roberts et al. |
| 4,846,199 | A | 7/1989 | Rose |
| 4,848,374 | A | 7/1989 | Chard et al. |
| 4,893,639 | A | 1/1990 | White |
| 4,907,606 | A | 3/1990 | Lilja et al. |
| 4,941,483 | A | 7/1990 | Ridings et al. |
| 4,944,317 | A | 7/1990 | Thal |
| 4,947,874 | A | 8/1990 | Brooks et al. |
| 4,947,875 | A | 8/1990 | Brooks et al. |
| 5,020,548 | A | 6/1991 | Farrier et al. |
| 5,027,836 | A | 7/1991 | Shannon et al. |
| 5,050,621 | A | 9/1991 | Creighton et al. |
| 5,060,671 | A | 10/1991 | Counts et al. |
| 5,065,776 | A | 11/1991 | Lawson et al. |
| 5,076,297 | A | 12/1991 | Farrier et al. |
| 5,105,831 | A | 4/1992 | Banerjee et al. |
| 5,105,838 | A | 4/1992 | White et al. |
| 5,144,962 | A | 9/1992 | Counts et al. |
| 720,007 | A | 2/1993 | Dexter |
| 5,183,062 | A | 2/1993 | Clearman et al. |
| 5,224,498 | A | 7/1993 | Deevi et al. |
| 5,249,586 | A | 10/1993 | Morgan et al. |
| 5,261,424 | A | 11/1993 | Sprinkel, Jr. |
| 5,269,327 | A | 12/1993 | Counts et al. |
| 5,322,075 | A | 6/1994 | Deevi et al. |
| 5,372,148 | A | 12/1994 | McCafferty et al. |
| 5,388,574 | A | 2/1995 | Ingebrethsen |
| 5,591,368 | A | 1/1997 | Fleischhauer et al. |
| 5,649,552 | A | 7/1997 | Cho et al. |
| 5,666,977 | A | 9/1997 | Higgins |
| 5,666,978 | A | 9/1997 | Counts et al. |
| 5,708,258 | A | 1/1998 | Counts et al. |
| 5,730,158 | A | 3/1998 | Collins et al. |
| 5,819,756 | A | 10/1998 | Mielordt |
| 5,845,649 | A | 12/1998 | Saito et al. |
| 5,865,185 | A | 2/1999 | Collins et al. |
| 5,934,289 | A | 8/1999 | Watkins et al. |
| 5,944,025 | A | 8/1999 | Cook et al. |
| 5,954,979 | A | 9/1999 | Counts et al. |
| 5,996,589 | A | 12/1999 | St. Charles |
| 6,053,176 | A | 4/2000 | Adams |
| 6,095,153 | A | 8/2000 | Kessler et al. |
| 6,125,853 | A | 10/2000 | Susa et al. |
| 6,155,268 | A | 12/2000 | Takeuchi |
| 6,164,287 | A * | 12/2000 | White ............. 131/328 |
| 6,349,728 | B1 | 2/2002 | Pham |
| 6,532,965 | B1 | 3/2003 | Abhulimen et al. |
| 6,536,442 | B2 | 3/2003 | St. Charles et al. |
| 6,598,607 | B2 | 7/2003 | Adiga et al. |
| 6,615,840 | B1 | 9/2003 | Fournier et al. |
| 6,655,379 | B2 | 12/2003 | Clark et al. |
| 6,688,313 | B2 | 2/2004 | Wren et al. |
| 6,772,756 | B2 | 8/2004 | Shayan |
| 6,803,545 | B2 | 10/2004 | Blake et al. |
| 6,805,545 | B2 | 10/2004 | Slaboden |
| 6,827,573 | B2 | 12/2004 | St. Charles et al. |
| 7,488,171 | B2 | 2/2009 | St. Charles et al. |
| 7,832,410 | B2 | 11/2010 | Hon |
| 2001/0015209 | A1 | 8/2001 | Zielke |
| 2001/0032643 | A1 | 10/2001 | Hochrainer et al. |
| 2003/0005926 | A1 | 1/2003 | Jones et al. |
| 2003/0150451 | A1 | 8/2003 | Shayan |
| 2003/0154991 | A1 | 8/2003 | Fournier et al. |
| 2004/0031495 | A1* | 2/2004 | Steinberg ............. 131/194 |
| 2004/0149296 | A1 | 8/2004 | Rostami et al. |
| 2004/0173229 | A1 | 9/2004 | Crooks et al. |
| 2004/0182403 | A1 | 9/2004 | Andersson et al. |
| 2004/0237974 | A1 | 12/2004 | Min |
| 2005/0016549 | A1 | 1/2005 | Banerjee et al. |
| 2005/0034723 | A1 | 2/2005 | Bennett et al. |
| 2005/0069831 | A1 | 3/2005 | St. Charles et al. |
| 2005/0090798 | A1 | 4/2005 | Clark et al. |
| 2005/0244521 | A1 | 11/2005 | Strickland et al. |
| 2005/0268911 | A1 | 12/2005 | Cross et al. |
| 2006/0191546 | A1 | 8/2006 | Takano et al. |
| 2006/0191548 | A1 | 8/2006 | Strickland et al. |
| 2006/0196518 | A1 | 9/2006 | Hon |
| 2007/0045288 | A1 | 3/2007 | Nelson |
| 2007/0074734 | A1 | 4/2007 | Braunshteya et al. |
| 2007/0102013 | A1 | 5/2007 | Adams et al. |
| 2007/0280652 | A1 | 12/2007 | Williams |
| 2007/0283972 | A1 | 12/2007 | Monsees |
| 2008/0149118 | A1 | 6/2008 | Oglesby et al. |
| 2009/0126745 | A1 | 5/2009 | Hon |
| 2009/0133691 | A1 | 5/2009 | Yamada et al. |
| 2009/0133703 | A1 | 5/2009 | Strickland et al. |
| 2009/0133704 | A1 | 5/2009 | Strickland et al. |
| 2009/0151717 | A1 | 6/2009 | Bowen |
| 2009/0260641 | A1 | 10/2009 | Monsees |
| 2009/0260642 | A1 | 10/2009 | Monsees |
| 2009/0272379 | A1 | 11/2009 | Thorens |
| 2010/0006092 | A1 | 1/2010 | Hale |
| 2011/0108023 | A1 | 5/2011 | McKinney |
| 2012/0247494 | A1 | 10/2012 | Oglesby et al. |
| 2013/0042865 | A1 | 2/2013 | Monsees |
| 2013/0312742 | A1 | 11/2013 | Monsees |
| 2014/0060552 | A1 | 3/2014 | Cohen et al. |

FOREIGN PATENT DOCUMENTS

| | | |
|---|---|---|
| DE | 4200639 | 7/1995 |
| DE | 19854005 A1 | 5/2000 |
| DE | 19854012 A1 | 5/2000 |
| EP | 0311581 A1 | 4/1989 |
| EP | 0430559 A2 | 6/1991 |
| EP | 0503767 A1 | 9/1992 |
| EP | 0532194 A1 | 3/1993 |
| EP | 0535695 | 4/1993 |
| ES | 2118034 A1 | 9/1998 |
| GB | 1025630 A | 4/1966 |
| GB | 1065678 | 4/1967 |
| IE | S2005-0051 | 2/2005 |
| IE | S2005-0563 | 8/2005 |
| IE | S2005-0615 | 9/2005 |
| JP | 61-108364 | 5/1986 |
| JP | 62-278975 | 12/1987 |
| JP | 64-37276 A | 2/1989 |
| JP | 2-124082 | 5/1990 |
| JP | 03-049671 | 4/1991 |
| JP | 05-115272 | 5/1993 |
| JP | 1993-115272 | 5/1993 |
| JP | 11-178563 | 6/1999 |
| JP | 2000-203639 | 7/2000 |
| JP | 2000-236865 | 9/2000 |
| JP | 1991-232481 | 10/2001 |
| JP | 2002-529111 | 9/2002 |
| JP | 2005-506080 | 3/2005 |
| KR | 0193885 B1 | 6/1999 |
| WO | WO-00-28842 A1 | 5/2000 |
| WO | WO-01-82725 A1 | 11/2001 |
| WO | WO-03-056948 A1 | 7/2003 |
| WO | WO-03-070031 A1 | 8/2003 |
| WO | WO 2004/064548 A1 | 8/2004 |
| WO | WO-2005-020726 A1 | 3/2005 |
| WO | WO-2006-015070 | 2/2006 |
| WO | WO-2006-082571 | 8/2006 |
| WO | WO-2007-012007 A2 | 1/2007 |
| WO | WO-2007-012007 A3 | 1/2007 |
| WO | WO-2007-026131 | 3/2007 |
| WO | WO-2007-039794 A2 | 4/2007 |
| WO | WO 2007-042941 | 4/2007 |
| WO | WO-2009-079641 A2 | 6/2009 |
| WO | WO-2009-079641 A3 | 6/2009 |
| WO | WO-2013-025921 A1 | 2/2013 |

OTHER PUBLICATIONS

Bombick et al., Chemical and biological studies of a new cigarette that primarily heats tobacco. Part 3. In vitro toxicology of whole smoke. Food and Chemical Toxicology. 1998; 36:191-197.

(56) References Cited

OTHER PUBLICATIONS

Borgerding et al. Chemical and biological studies of a new cigarette that primarily heats tobacco. Part 1. Chemical composition of mainstream smoke. Food and Chemical Toxicology. 1997; 36:169-182.
PCT/US08/087488 Search Report dated Jul. 13, 2009.
"Lighter." Merriam-Webster Online Dictionary. 2009. Merriam-Webster Online. Jun. 8, 2009 [http://www.merriam-webster.com/dictionary/lighter].
Australian Application 2008338305 Exam Report dated Jul. 29, 2011.
Australian Application 2008338305 Exam Report dated Mar. 20, 2013.
Baker et al., "The pyrolysis of tobacco ingredients," J. Anal. Appl. Pyrolysis, vol. 71, pp. 223-311 (2004).
Canadian Application No. 2,616,120 Office Action dated Feb. 4, 2013.
Canadian Application 2,712,469 Exam Report dated Oct. 27, 2011.
Canadian Patent Application 2,712,469 Office Action dated Jul. 4, 2012.
Canadian Patent Application 2,712,469 Office Action dated May 16, 2013.
Canadian Patent Application 2,712,469 Office Action dated Dec. 18, 2013.
Chinese Patent Application 200680026317 Exam Report dated Jan. 31, 2012.
Chinese Patent Application 200680026317 Office Action issued Aug. 27, 2012.
Chinese Patent Application 200880126977 Office Action issued Aug. 28, 2012.
Chinese Patent Application 200680026317.6 Rejection Decision dated Dec. 24, 2012.
Chinese Patent Application 200680026317.6 Office Action dated Oct. 8, 2013.
Chinese Patent Application 200880126977 Office Action issued May 29, 2013.
European Patent Application 06787864.5 Exam Report dated Mar. 22, 2013.
European Patent Application 06787864.5 Exam Report dated Nov. 12, 2013.
European Patent Application 08860921.9 Extended Search Report issued Oct. 10, 2013.
Ingebrethsen et al., "Electronic Cigarette aerosol particle size distribution measurements", Inhalation Toxicology, 2012; 24 (14): 976-984.
Japanese Patent Application 2008-522926 Exam Report dated Nov. 29, 2011.
Japanese Patent Application 2010-539818 Notification of Reasons for Refusal dated Apr. 23, 2013.
Korean Patent Application 10-2008-7003419 Office Action dated Feb. 7, 2013.
Korean Patent Application 10-2010-7016086 Office Action dated Mar. 25, 2013.
Korean Patent Application 10-2010-7016086 Office Action dated May 8, 2012.
Korean Patent Application 10-2008-7003419 Office Action dated Nov. 25, 2013.
Korean Patent Application 10-2010-7016086 Final Rejection dated Dec. 30, 2013.
PCT/IB2006/002040 International Preliminary Report on Patentability dated Apr. 1, 2008.
PCT/IB2006/002040 International Search Report and Written Opinion dated Mar. 26, 2007.
PCT/IB2006/003842 International Preliminary Report on Patentability dated Apr. 1, 2008.
PCT/IB2006/003842 International Search Report and Written Opinion dated May 31, 2007.
PCT/US2012/051165 International Search Report and Written Opinion dated Oct. 25, 2012.
Torikai et al., "Effects of temperature, atmosphere and pH on the generation of smoke compounds during tobacco pyrolysis," Food and Chemical Toxicology 42 (2004) 1409-1417.
TW 097149447 Office Action issued Nov. 11, 2013.
U.S. Appl. No. 12/336,439 Final Office Action dated Feb. 1, 2012.
U.S. Appl. No. 12/336,439 Office Action dated Aug. 17, 2011.
U.S. Appl. No. 12/482,379 Non Final Office Action mailed Dec. 17, 2013.
U.S. Appl. No. 12/482,379 Final Office Action mailed Sep. 5, 2012.
U.S. Appl. No. 12/482,379 Office Action mailed Dec. 22, 2011.
U.S. Appl. No. 11/485,168 Final Office Action mailed Sep. 5, 2013.
U.S. Appl. No. 11/485,168 Office Action mailed Dec. 21, 2012.
U.S. Appl. No. 12/336,439 Office Action mailed Feb. 22, 2013.
U.S. Appl. No. 12/336,439 Final Action dated Nov. 25, 2013.
Australian Application 2006269882 Exam Report dated Nov. 29, 2010.
Australian Application 2012202592 Exam Report dated Dec. 10, 2013.
Canadian Application No. 2,616,120 Office Action dated Jan. 3, 2014.
Canadian Patent Application 2,712,469 Office Action dated Oct. 27, 2011.
Chinese Patent Application 200880126977 Office Action issued Dec. 11, 2013.
Davis & Nielsen, "Marketing, Processing and Storage: Green Leaf Threshing and Redrying Tobacco," Tobacco Production, Chemistry and Technology, (1999) Section 10B, pp. 330-333, Bill Ward, Expert Leaf Tobacco Company, Wilson, North Carolina, USA.
Japanese Patent Application 2012-106389 Office Action dated Sep. 24, 2013.
PCT/US06/28039 International Search Report dated Sep. 6, 2007.
PCT/US08/87488 IPER and Written Opinion dated Jun. 22, 2010.
PCT/US06/28039 IPER and Written Opinion dated Jul. 15, 2008.
Canadian Patent Application 153084 Office action dated Mar. 27, 2014.
Chinese Patent Application 200680026317.6 Office Action dated Jan. 26, 2014.
Chinese Patent Application 201210129768 Office Action dated Feb. 25, 2014.
Japanese Patent Application 2010-539818 dated Mar. 24, 2014.
PCT/US2012/051165 International Preliminary Report on Patentability dated Feb. 18, 2014.
U.S. Appl. No. 11/485,168 Office Action mailed Mar. 27, 2014.
Wells. "Glycerin as a Constituent of Cosmetics and Toilet Preparations." Journal of the Society of Cosmetic Chemists,1958; 9(1): 19-25.
European Patent Application 06787864.5 Extended European Search Report completed Mar. 22, 2013.
Korean Patent Application 10-2010-7016086 Office Action dated May 8, 2012 (non-English and English translation).
Kuo et al. Applications of Turbulent and Multiphase Combustion, Appendix D: Particle Size-U.S. Sieve Size and Tyler Screen Mesh Equivalents, 2012, p. 541-543.
McCann et al., "Detection of carcinogens as mutagens in the *Salmonella*/microsome test: Assay of 300 chemicals: discussion." Proct. Nat. Acad. Sci, USA, Mar. 1976, vol. 73 (3), 950-954.
PCT/US06/28039 *Corrected* Written Opinion dated Dec. 20, 2007.
PCT/US2008/87488 Written Opinion Jul. 13, 2009.
U.S. Appl. No. 11/485,168 Non-Final Office Action mailed Jun. 23, 2009.
U.S. Appl. No. 11/485,168 Final Office Action mailed Nov. 3, 2009.
U.S. Appl. No. 11/485,168 Office Action mailed Feb. 4, 2010.
U.S. Appl. No. 11/485,168 Final Office Action mailed Aug. 3, 2010.
European Search Report dated Jun. 13, 2014 for EP Application No. 13189967.6.
Office action dated Jul. 1, 2014 for AU Application No. 2013205041.
Office action dated Jul. 9, 2014 for U.S. Appl. No. 11/485,168.
Office action dated Jul. 23, 2014 for CA Application No. 2,712,469.
Office action dated Aug. 6, 2014 for U.S. Appl. No. 12/336,439.

\* cited by examiner

METHOD AND SYSTEM FOR VAPORIZATION OF A SUBSTANCE

CROSS-REFERENCE

This application is a divisional application of Ser. No. 11/485,168, filed Jul. 11, 2006, which is incorporated herein by reference in its entirety, and to which application we claim priority under 35 USC §121. This application also claims the benefit of U.S. Provisional Application No. 60/700,105, filed Jul. 19, 2005, which application is incorporated herein by reference.

BACKGROUND OF THE INVENTION

1. Field of the Invention

The present invention is directed to improvements in smoking devices, particularly to smoking articles which employ a formed tobacco cartridge as a source of producing vapor by heat transfer to the cartridge by conduction, convection, and radiation for smoke and flavor. The present invention relates to self-contained vaporization devices, and more particularly, to a low-temperature vaporization device for use of tobacco product. The device is of an elongated main body with a mouthpiece at one end and an attached tubular casing at the other end having a vaporization chamber and a heater. The mouthpiece and the casing form an unitary unit.

2. Description of the Related Art

Smoking devices, such as cigarette holders and pipes are well known in the art for providing flavored vapor from a smokable substance to a user for therapeutic and smoking pleasure. However, existing devices used have no control of heating and combustion of the tobacco products. The devices tend to produce toxic, tarry and carcinogenic by-products which are harmful and also impart a bitter and burnt taste to a mouth of a user.

A further problem is that there is no control of contamination of the inhaled vapor mixture with heater exhaust gases, due to inappropriate proportioning and location of the inlets and the exhaust vents. Typically, the exhaust gas is used to directly heat the tobacco, and those gases contain harmful byproducts of incomplete combustion.

In an effort to overcome these deficiencies, there have been numerous attempts to provide a device structure and the substance for producing vapor for smoking which is free from harmful by-product and would provide a cool and soothing vapor for smoking.

For example, U.S. Patent Application No. 2004/0237974 A1, published on Dec. 2, 2004 for Min discloses a filtering cigarette and cigar holder which removes tar and nicotine from the tobacco smoke.

U.S. Patent Application No. 2004/0031495 A1, published on Feb. 19, 2004 for Steinberg discloses a vaporization pipe with flame filter which uses a flame to vaporize the smoking substance.

U.S. Pat. No. 6,164,287, issued Dec. 26, 2000 to White, describes a smoking device which produces smoke from tobacco at low temperatures, without producing harmful byproducts.

U.S. Pat. No. 4,848,374, issued Jul. 18, 1989 to Chard et al describe a smoking device to vaporize aerosol precursor, an event which precedes condensation to mainstream aerosol precursor by contact with heated surface rather than by hot gases into the mouth of a smoker.

U.S. Pat. No. 4,219,032, issued Aug. 26, 1980 to Tabatznik et al describe a smoking device wherein an extracted smoke is cooled by passing it through a suitable liquid to provide a soothing smoke.

U.S. Pat. No. 4,020,853, issued May 3, 1977 to Nuttall, describes a smoking pipe made of ceramic material such as colored and ornamental porcelain for enhancing the artistic look, and also to provide a circulating air to keep the outer wall of the pipe cool and safe for handling.

U.S. Pat. No. 3,792,704, issued Feb. 19, 1974 to Parker, describes a pipe tobacco smoking system, wherein the pipe and the tobacco capsule are mutually designed to yield a slim-line smoking combination that can be manufactured from relatively low temperature thermoplastic material.

SUMMARY OF THE INVENTION

The present invention is drawn to a novel smoking device consisting of a mouthpiece and a casing having a heater, a low temperature vaporization chamber, a fuel tank, an igniter with control means for maintaining equilibrium point by keeping the operating temperature below 400 F, preferably below 350 F during combustion whereby in order to maintain a stable operating temperature, a thermal regulator is used to control flow rate of the fuel.

Accordingly, it is principal object of the invention to provide a mouthpiece made of a high temperature food-safe material, such as ceramic, glass, or high temperature plastics known as PEI resin (brand name Ultem). However, suitable plastic or wood, etc., could also be used but would additionally require an insulating material that would prevent excessive heat reaching the user's lips.

Additionally, air inlets are directed downwards, so that fresh ambient air drawn through mixes with the vapor generated into the vaporization chamber located above the smokable substance cartridge, which is extracted from the cartridge by inlets located below the cartridge and drawn into user's mouth for inhalation.

It is another object of the invention to provide air inlet or inlets having a diameter and direction sized to admit ambient air into the chamber to heat up the substance and not effect the operating temperature and also regulating the velocity of ambient air entering and mixing with the vapor generated from combustion, radiation and convection in the chamber at such a rate that the proportionate inhalation passage provides a perception to the user as if the smoke is drawn through a cigarette.

It is still another object of the invention to provide a heater which is separated from the vapor chamber by an insulating medium such as ring made of PTFE, ceramic or other insulating material and thereby preventing the exhaust gases produced by the heater from entering and contaminating the vapor in the vaporization chamber collected for inhalation.

Another object of the invention to provide a heater is formed of a conductive shell and a catalyst, the shell may be of one or more material formed by welding or pressing together. Whereas, the catalyst could be of platinum or palladium impregnated metal or glass or other suitable material, which provides for efficient flameless combustion of the fuel and glows red when heated to indicate that the device is activated. Additionally, a feedback loop could be employed to regulate the desired temperature.

Preferably the tobacco cartridge formed and shaped for easier insertion into the heating chamber and to snugly fit into the cavity of the heating chamber for improved thermal conduction and vaporization. The cartridges are formed and wrapped into wrapper which does not produce significant amount of harmful gases.

These and other objects of the present invention will become readily apparent upon further review of the following specifications and drawings.

DETAILED DESCRIPTION OF THE INVENTION

Figure 1:
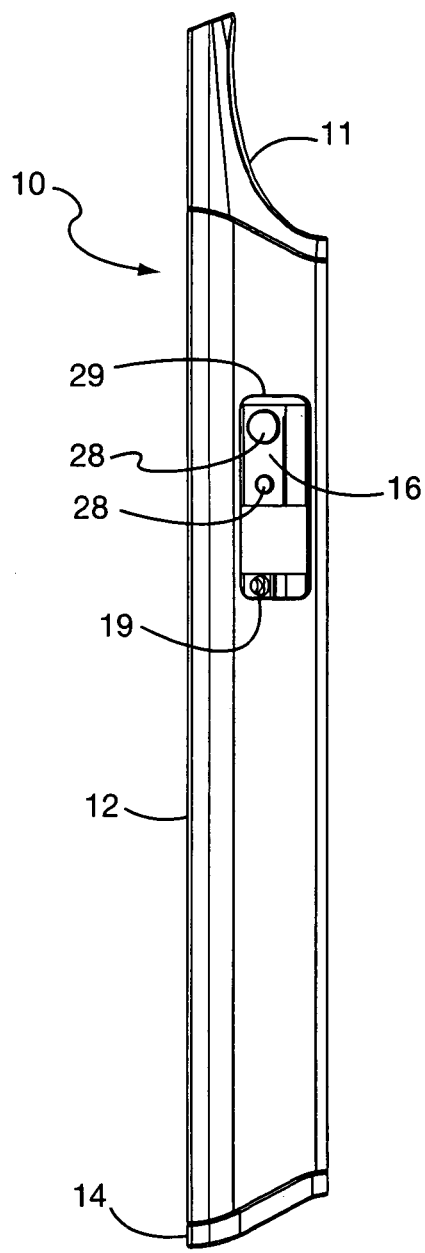
FIG. 1 is a side view of a portable vaporization device, according to a preferred embodiment of the present invention.
Figure 2:
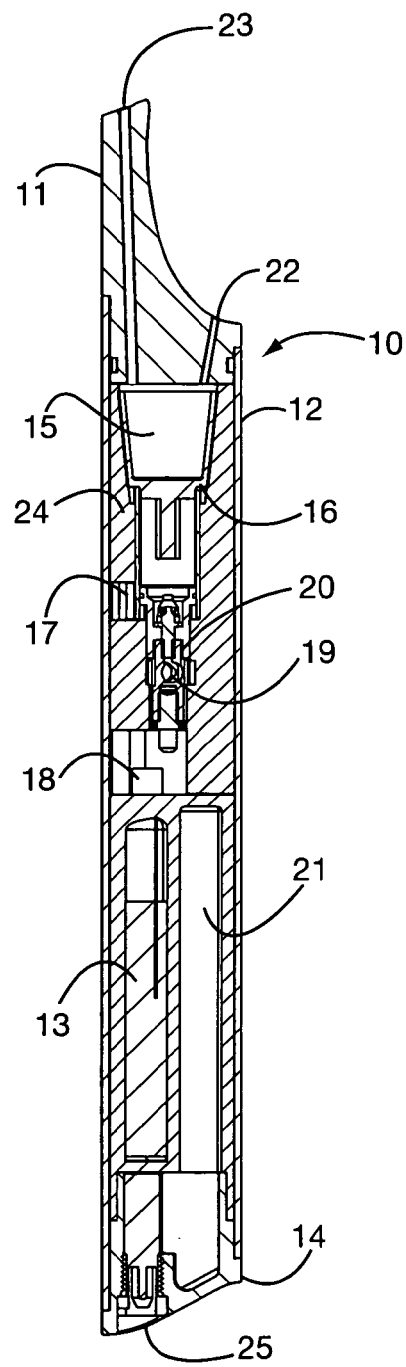
FIG. 2 is a sectional view of the same embodiment.

Referring to FIG. 1 and FIG. 2, the exterior of the device 10 comprises a mouthpiece 11, a tubular case 12, and the base 14 of a butane tank 21. The mouthpiece is removable and creates an airtight seal with the interior of the case. With the mouthpiece removed, a tobacco cartridge (FIG. 5) is introduced to vaporization chamber 15 of a heater 16. The mouthpiece is then reinserted to close the device.

The mouthpiece is made of a high-temperature and food-safe material such as ceramic, glass, or various high-temperature plastics such as PEI resin (brand name Ultem). Design is simplified by use of high temperature materials, but standard plastics or wood, etc, could also be used with the addition of an insulating component that prevents any excessive heat from reaching the user's lips.

To activate the device, the butane tank is pulled axially outward, partially removing it from the case. This starts the flow of butane by opening a master valve 18, and then activating a piezoelectric igniter 13. The tank remains in the partially removed position for the duration of use. While the master valve is open, butane flows through a thermal regulator 17, and into the carburetor 20. Ambient air enters the case through slot 19. A venturi in the carburetor entrains air, causing it to mix with the butane. The mixture then flows into the heater 16.

The lead of the ignitor is positioned in the heater. With the spark of the ignitor (immediately following the start of gas flow) the gas ignites and heat starts conducting throughout the heater. Heat transfers to the cartridge by conduction, convection, and radiation. The cartridge is shaped to fill the chamber, so as to maximize surface contact for thermal conduction.

As the cartridge heats, vapor generates within the cartridge and in the space immediately above it. When a user draws on the device, fresh air enters through air inlet 22, mixes with the vapor, and the mixture is delivered to the user via the inhalation passage 23. In the preferred embodiment, the air inlet or inlets are directed downward, so as to improve the extraction of vapor from the cartridge. They could also be directed along a diagonal through the mouthpiece, or laterally through the case itself, above the cartridge.

Figure 3:
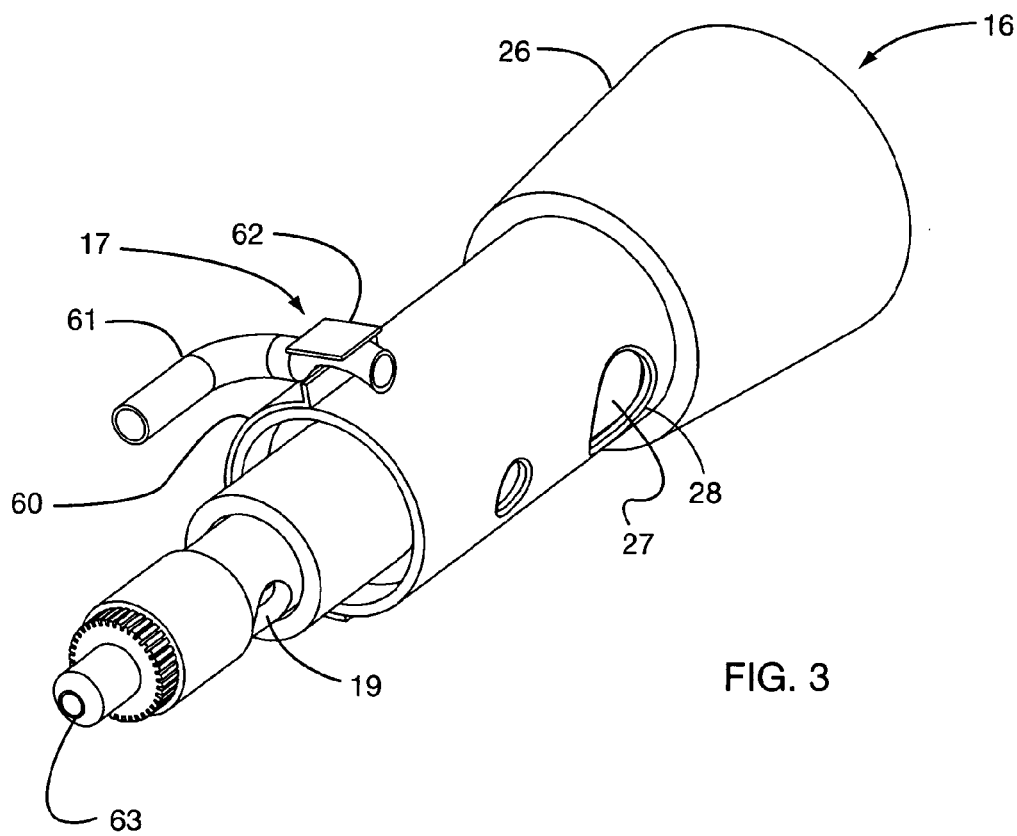
FIG. 3 is a perspective view of a heater, according to the same embodiment.

FIG. 3 depicts a detailed view of the heater 16. The heater comprises a thermally conductive shell 26 and catalyst 27. The shell could be comprised of one material, or a combination of materials welded or pressed together. The catalyst could be platinum- or palladium-impregnated metal or glass, or other suitable material known to those skilled in the art. The catalyst provides for efficient flame-less combustion of the butane. The vent 28 of the heater is positioned such that it is visible through the slot 29 of the body as shown in FIG. 1. This allows the user to see the catalyst which, when heated, can glow red to indicate that the device has been activated.

Referring again to FIG. 3, adjacent to the heater and in intimate thermal contact is the thermal regulator 17. As the temperature of the heater increases, so does that of the regulator. The regulator is designed to restrict the flow of butane as the temperature increases, thus creating a feedback loop. In the preferred embodiment, the regulator consists of a bimetallic strip 60 and silicone tubing 61 which is the conduit of the butane. The two are arranged such that as the bimetallic strip heats up, it curls to pinch the silicone tube and thereby restrict the flow of butane. The reduced flow of butane results in less heat generated. The heater subsequently cools down, and so does the regulator, allowing more butane to flow again. The overall result is that a stable operating temperature is established in the heater. Such a system can be readily tuned to achieve an operating temperature that varies by less than +/−5 degrees Fahrenheit.

The regulator further comprises a moveable backplate 62 which allows adjustability of the operating temperature by adjusting the temperature at which the bi-metallic actuator closes the tube valve. This is to be performed once at manufacture, to calibrate the device. In alternate embodiments, a control means could be used to allow the target temperature of the device changed during operation.

In the preferred embodiment, the regulator comprises in part a bi-metallic strip and silicone tubing valve. In alternate embodiments, the regulator could be comprised of other materials and configurations, as described later.

For the purposes of vaporizing most botanicals in this device, the desired operating temperature is below 400 F; preferably below 350 F.

In the preferred embodiment, the air inlet diameter is sized such that inhalation is somewhat inhibited. This allows time for ambient air entering the chamber to heat up and not affect operating temperature considerably. It also increases velocity of the entering air, which improves circulation and mixing in the vaporization chamber. It also creates a partial vacuum, lowering the vapor point temperature for material contained in the vaporization chamber. The reduction in draw rate can also serve to give the impression of drawing on a cigarette or pipe. Both the fresh air inlet and inhalation passage can be adjusted to provide appropriate draw rate for the operating temperature of the device, and the perception intended for the user.

Once the cartridge is consumed, the device is turned off by pushing the tank back into the case, closing the master valve. The spent tobacco cartridge is removed by opening the device and turning the body over. In the preferred embodiment, the cartridge simply falls out. In alternate embodiments, a mechanism could be used to quickly and easily remove the cartridge. This mechanism could include, but does not require, the use of a pin or slide part to eject the cartridge as another part of the device is moved or removed. The removal mechanism could also involve introduction of a foreign object.

In an alternate embodiment, the mouthpiece is permanently attached to the body. In that case, the vaporization chamber could be accessed by operating a sliding or hinged door, or similar means, built into the device.

The heater of the device is fitted into the case with an insulator 24. The insulator could be made of PEI (brand name Ultem), ceramic, or other insulating material. The insulator serves to minimize thermal transfer from the heater to the case, while creating an air-tight seal. The seal prevents exhaust gases produced by the heater from entering the vaporization chamber. Exhaust gases are instead vented out the case slots. Since the air inlet is distant from the slots, there is substantially no contamination of the inhaled vapor mixture by heater exhaust gases.

In an alternate embodiment, the insulator could be a partially hollow shell, containing a sealed vacuum. In another embodiment, the heater might be sealed directly to the case by braising in a vacuum furnace, so as to create a vacuum between the two and obviate need for an insulator component.

In the preferred embodiment, the tank is made of a translucent material. This allows the user to determine the level of fuel remaining by looking at the base of the tank.

In the preferred embodiment, the case is made of a material that is either a good thermal conductor (such as aluminum), or a poor one (such as ceramics). In both cases, the effect is that the body remains cool enough to touch over a large portion of its surface.

In the preferred embodiment, a bimetallic actuator is used in the regulator. In alternate embodiments, a shape memory alloy actuator such nickel-titanium alloys ("Nitinol") could be used. Alternatively, a paraffin-filled component that expands and contracts to modulate butane flow could be employed. Alternatively, a system could be employed to measure the current temperature, e.g., with a thermocouple sensor and compare it to a prescribed temperature, e.g., with a microcontroller, and by controlling an electromechanical valve, e.g., servo or solenoid valve. In an embodiment with user-selected temperature, as described above, the selected temperature could be used as an input to this system.

In the preferred embodiment, a thermal regulator is used. In an alternate embodiment, the device is constructed without an active regulating element. This could result in reduced complexity and in lowering the overall cost of the device. In this case, the flow of butane is set at a low level. In use, the temperature inside the chamber increases until an equilibrium point where additional heat introduced equals the heat lost to the environment. Heat is lost by conduction through the body of the device, and with the vapor delivered to the user. This equilibrium point determines the operating temperature of the device. By changing the butane flow rate, size and material of the burner, and other factors, the system can be calibrated to provide a fairly stable desired operating temperature.

The principal advantage of the preferred bimetallic regulator feedback loop methods over the equilibrium method is that the operating temperature is not dependent on environmental factors such as ambient temperature and wind.

In the preferred embodiment, a piezo-electric ignitor is used. Other igniters could be used, such as, a flint starter or battery-powered resistive coil.

In the preferred embodiment, the butane tank is meant to be refillable, and has a port 25 for that purpose. As an alternate embodiment, the tank might be disposable once its fuel is exhausted. A release mechanism such as a pin or cam would be employed allowing the user to quickly remove the depleted tank and replace it with a full one. The replaceable tank might include additional parts of the device including, but not limited to, the ignitor and heater. Butane is the preferred fuel source, but could be replaced by other liquid fuels, such as ethanol.

In alternate embodiments of the present invention, various means of feedback could be used to indicate the following states or metrics of the device: 1) the device is on, 2) the current temperature of the vaporization chamber, 3) the chamber is below a prescribed operating temperature, 4) the chamber has reached a prescribed operating temperature and vapor is ready for consumption, and 5) the chamber has exceeded a prescribed operating temperature.

The means of the feedback includes both physical and electronic implementations. Possibilities include thermochromatic paint, light-emitting diodes and liquid crystal display. The sensing and control means for electronic feedback could be implemented by use of thermocouple and microcontroller, as is known to those skilled in the art.

Active elements contained in botanicals vaporize at different temperatures. In the preferred embodiment, the device is calibrated to establish a single stable temperature, intended for vaporizing solely tobacco or solely chamomile, for example. In alternate embodiments, a control means would be used to select a variety of temperature settings. The user would choose which setting based on the type of cartridge used. The control means could effect a desired temperature mechanically, such as by changing flow rate of the valve, or electronically, such as by electromechanical valve and microcontroller intermediary.

Butane was found to be the most energy-dense and practical fuel source. In alternate embodiments of the invention, the butane heating system is replaced by a battery-powered electric heater or other compact heat source.

Figure 4:
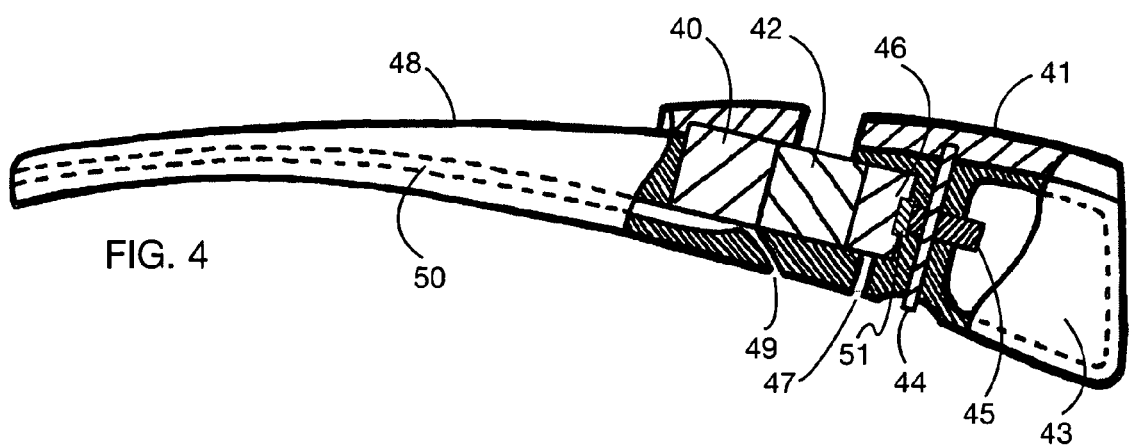
FIG. 4 is a cutaway view of an alternate embodiment according to the present invention.

FIG. 4 depicts a cutaway view of an alternate embodiment which more closely resembles a traditional pipe form. In this embodiment the device retains all of the critical elements from the preferred embodiment. The user inserts a tobacco cartridge 40, under a sliding top piece 41, where the cartridge mates with the heater 42. Fuel held in the tank 43 is released by turning dial 44 to open master valve 45. The fuel travels through the regulator 51, and then through the carburetor 46 where it draws in air through the intake port 47 and catalyzes in a manner similar to that of the preferred embodiment. As the cartridge 40 reaches its operating temperature the user places the mouthpiece 48 in their mouth and draws air in through the inhalation intake port 49 and through the vapor passage 50 where it is pre-cooled.

Figure 5:
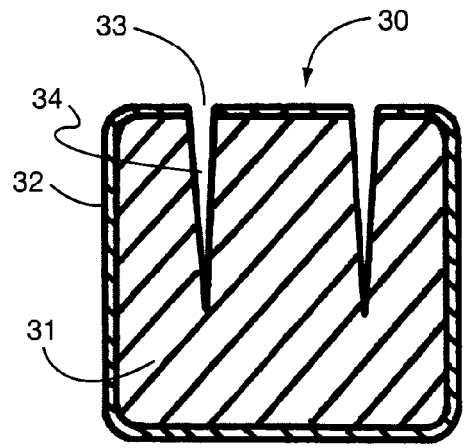
FIG. 5 is a sectional detail view of a tobacco cartridge, according to the preferred embodiment.

FIG. 5 depicts a sectional view of the tobacco cartridge 30. In the preferred embodiment, it consists of tobacco material 31, enclosed in a wrapper 32, with perforations 33, and aeration wells 34. The wrapped cartridge allows for the easy insertion and disposal of tobacco material without creating a mess, while the perforations allow the formed vapor to be released. When the cartridge is used up it can be easily disposed of in its entirety.

Here, tobacco or tobacco material is defined as any combination of natural and synthetic material that can be vaporized for pleasure or medicinal use. As an example, one test cartridge was prepared as embodiment of the present invention using flue-cured tobacco, glycerin, and flavorings. Those skilled in the art of tobacco product manufacture are familiar with these and other ingredients used for cigarettes, cigars, and the like. The test cartridge was produced by chopping tobacco into fine pieces (less than 3 mm diameter, preferably less than 2 mm), adding the other ingredients, and mixing until even consistency was achieved.

In the preferred embodiment, the cartridge is primarily cylindrical. In other embodiments, the form could be modified for various reasons. As an example, the walls of the cartridge might be drafted for easier insertion into the vaporization chamber. Or, the bottom of the cartridge might possess receptacles, which when combined with complimentary features on the surface cavity of the vaporization chamber would allow for more surface contact and hence improved thermal conduction.

Figure 6:
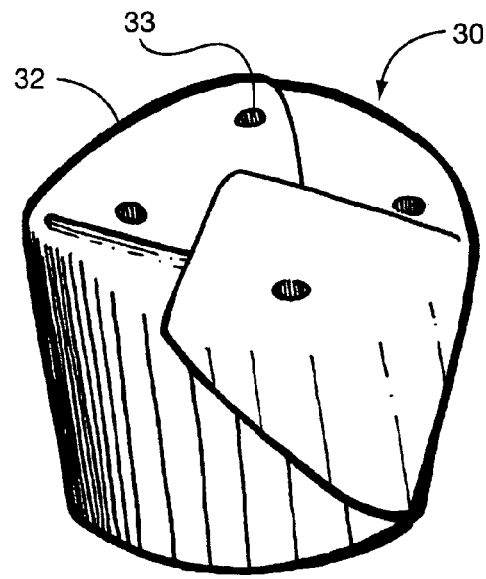
FIG. 6 is a perspective view of a tobacco cartridge, according to the preferred embodiment.

Any material could be used for the wrapper, provided that when heated to the operating temperature, it does not produce significant amounts of harmful gases. Aluminum foil and parchment paper are two examples. With papers, the cartridge would be manufactured in a folded-cup design, similar to that shown in FIG. 6. With films or metal foils, the wrapper could be pressed or blow-molded to the appropriate shape.

During manufacture of the preferred embodiment, the cartridge is enclosed on all sides, and perforated on the top so that vapors can emanate upwards. In the perforation step, or in an additional step, the optional aeration wells would be created.

Figure 7:
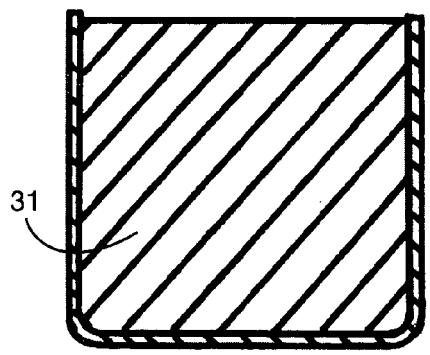
FIG. 7 is a sectional detail view of a tobacco cartridge, according to an alternate embodiment.

In an alternate embodiment, the cartridge might be wrapped on all sides but leaving the top exposed, as shown in FIG. 7. This is possible since the purpose of the wrapper is primarily to prevent tobacco material from touching the sides and bottom of the vaporization chamber.

In another embodiment, the material for the top of the cartridge might be vapor-permeable, such that perforations are not necessary.

In another embodiment, the cartridge as purchased by the user has no openings, but is punctured prior to insertion into the device, or upon introduction to the vaporization device. The latter could be achieved by adding a hollow puncturing means to the mouthpiece part of the device. For example, the inhalation passage of the mouthpiece could be extended by a hollow tube. When the mouthpiece is reinserted to close the device, it pierces the cartridge previously introduced, and allows a path for vapor to exit to the user.

Figure 8:
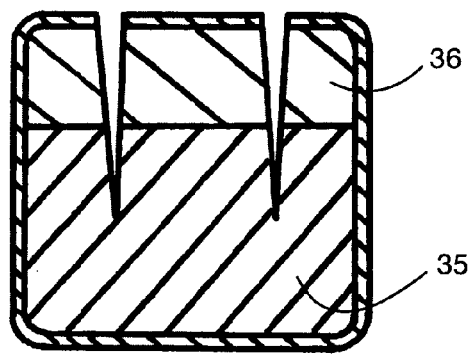
FIG. 8 is a sectional detail view of a tobacco cartridge, according to an alternate embodiment.

In the preferred embodiment, the tobacco material is a homogenous mixture. In another embodiment, there might be two layers, as shown in FIG. 8. The moist layer 35 has higher content of vapor-forming material than the dry layer 36, which consists of dry tobacco or other material acting as a filter. The dry layer serves to prevent any liquid from bubbling up and out of the cartridge during heating.

In another embodiment of the cartridge, a lower compartment might consist entirely of a vapor-forming medium, such as glycerine. An upper region would consist of the tobacco material to be vaporized, and the two would be separated by a material that only allows the medium to pass in a vapor or gaseous phase. Gore-tex (brand name) is one such material. In use, vapor generated in the lower region would pass through the semi-permeable membrane, volatize the active components of the tobacco, and a mix of the two would be delivered to the user upon inhalation.

In another embodiment, the consistency of the tobacco material is such that the wrapper is not necessary. This is possible if at least the outer surface of the cartridge is dry and cohesive enough to not leave deposits inside the device. Such a cartridge can be made by forming tobacco material in a mold. If the resulting surface is excessively moist, it can be dried by heating the cartridge in an oven.

It is to be understood that the present invention is not limited to the embodiments described above, but encompasses any and all embodiments within the scope of the following claims.

What is claimed is:

1. A device for generating an inhalable vapor, the device comprising:
   a casing comprising a heater having a vaporization chamber to hold a smokable material in a cartridge; and
   a mouthpiece for use in connection with the casing, the mouthpiece comprising an air inlet for entry of fresh air into the casing and a hollow tube comprising an inhalation passage, the hollow tube extends into the vaporization chamber for releasing the inhalable vapor generated within the casing through the inhalation passage to a user.

2. The device of claim 1, wherein said air inlet is directed downwards.

3. The device of claim 1, wherein said air inlet is directed along a diagonal through the mouthpiece.

4. The device of claim 1, wherein said hollow tube comprises a puncturing means.

5. The device of claim 1, wherein the vaporization chamber is accessed through a door.

6. The device of claim 1, wherein the heater is electric or battery-powered.

7. The device of claim 1 further comprising a fuel source for the heater.

8. The device of claim 7 wherein the fuel source is butane.

9. The device of claim 7, wherein one or more of the fuel source, the mouthpiece and the cartridge are configured for removal from the device.

* * * * *